(12) United States Patent
Yu et al.

(10) Patent No.: US 11,001,866 B2
(45) Date of Patent: May 11, 2021

(54) BURKHOLDERIA AND APPLICATIONS THEREOF

(71) Applicants: JIANGSU AOSAIKANG PHARMACEUTICAL CO., LTD., Nanjing (CN); EAST CHINA UNIVERSITY OF SCIENCE AND TECHNOLOGY, Shanghai (CN)

(72) Inventors: Huilei Yu, Shanghai (CN); Qian Zhao, Nanjing (CN); Yan Zhang, Nanjing (CN); Jiang Pan, Nanjing (CN); Jianhe Xu, Nanjing (CN)

(73) Assignees: JIANGSU AOSAIKANG PHARMACEUTICAL CO., LTD., Nanjing (CN); EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 0 days.

(21) Appl. No.: 16/620,529

(22) PCT Filed: Oct. 25, 2017

(86) PCT No.: PCT/CN2017/107682
§ 371 (c)(1),
(2) Date: Dec. 9, 2019

(87) PCT Pub. No.: WO2019/056467
PCT Pub. Date: Mar. 28, 2019

(65) Prior Publication Data
US 2020/0385770 A1   Dec. 10, 2020

(30) Foreign Application Priority Data

Sep. 20, 2017 (CN) .......................... 201710857192.1

(51) Int. Cl.
*C12P 17/16* (2006.01)
*C12R 1/01* (2006.01)

(52) U.S. Cl.
CPC .............. *C12P 17/165* (2013.01); *C12R 1/01* (2013.01)

(58) Field of Classification Search
CPC combination set(s) only.
See application file for complete search history.

(56) References Cited

U.S. PATENT DOCUMENTS 5,840,552 A   11/1998   Holt et al.

FOREIGN PATENT DOCUMENTS

| CN | 101372676 A | 2/2009 |
|---|---|---|
| CN | 103045504 A | 4/2013 |
| CN | 106191193 A | 12/2016 |
| CN | 106947719 A | 7/2017 |
| WO | 03020890 A2 | 3/2003 |

OTHER PUBLICATIONS

Peter Babiak et al, Whole-cell oxidation of omeprazole sulfide to enantiopure esomeprazole with *Lysinibacillus* sp B71, Bioresource Technology, 2011, 7621-7626.
Zhimei Yuan et al., Cloning and Expression of Pseudomonas Monooxygenase Genes and Its Activity Analysis in Biocatalysis of Chiral Sulfoxide, Genomics and Applied Biology, Dec. 31, 2016, p. 886-891, Vol.35, No. 4, ISSN:1674-568X.
Yongzheng Chen et al., Stereoselective oxidation of sulfides to optically active sulfoxides with resting cells of Pseudomonas monteilii CCTCC M2013683, Journal of Molecular Catalysis B: Enzymatic, May 20, 2014, p. 100-104, vol. 106, ISSN: 1381-1177.

*Primary Examiner* — Heidi Reese
(74) *Attorney, Agent, or Firm* — Bayramoglu Law Offices LLC

(57) ABSTRACT

A strain of *Burkholderia* is *Burkholderia glathei* ECU0712, with an accession number of CGMCC NO. 14464. With the strain or its extract as the biocatalyst, thioether is catalyzed to be oxidized asymmetrically to chiral sulfoxide, with significant advantages that the obtained product has a high optical purity, and benefits of a simple reaction system, short preparation time of the catalyst and a high yield of the product.

13 Claims, 2 Drawing Sheets
Specification includes a Sequence Listing.

SEQUENCE LISTING

<160> NUMBER OF SEQ ID NOS: 1

<210> SEQ ID NO 1
<211> LENGTH: 1422
<212> TYPE: DNA
<213> ORGANISM: Burkholderia glathei CGMCC14464

<400> SEQUENCE: 1

```
tggctcagat tgaacgctgg cggcatgcct tacacatgca agtcgaacgg cagcacgggg      60
gcatccctgg tggcgagtgg cgaacgggtg agtaatacat cggaacgtgt cctgtagtgg    120
```

```
gggatagccg gcgaaagccg gattaatacc gcatacgatc tacggaagaa agcgggggat    180
cttcggacct cgcgctatag gggcggccga tggcagatta gctagttggt ggggtaaagg    240
cctaccaagg cgacgatctg tagctggtct gagaggacga ccagccacac tgggactgag    300
acacggccca gactcctacg ggaggcagca gtggggaatt ttggacaatg ggggaaaccc    360
tgatccagca atgccgcgtg tgtgaagaag gccttcgggt tgtaaagcac ttttgtccgg    420
aaagaaaact tcggggctaa tacctctgga ggatgacggt accggaagaa taagcaccgg    480
ctaactacgt gccagcagcc gcggtaatac gtagggtgcg agcgttaatc ggaattactg    540
ggcgtaaagc gtgcgcaggc ggtctgttaa gacagatgtg aaatcccggg gcttaacctg    600
ggaactgcat ttgtgactag caggctagag tatggcagag gggggtagaa ttccacgtgt    660
agcagtgaaa tgcgtagaga tgtggaggaa taccgatggc gaaggcagcc ccctgggcca    720
atactgacgc tcatgcacga aagcgtgggg agcaaacagg attagatacc ctggtagtcc    780
acgccctaaa cgatgtcaac tagttgttgg ggattcattt ccttagtaac gtacgtaacg    840
cgtgaagttg accgcctggg gagtacggtc gcaagattaa aactcaaagg aattgacggg    900
gacccgcaca agcggtggat gatgtggatt aattcgatgc aacgcgaaaa accttaccta    960
cccttgacat ggtcggaacc ctggtgagag ctggggggtgc tcgaaagaga accgacacac   1020
aggtgctgca tggctgtcgt cagctcgtgt cgtgagatgt tgggttaagt cccgcaacga   1080
gcgcaaccct tgtccttagt tcgtacgtaa gagcactcta aggagactgc cggtgacaaa   1140
ccggaggaag gtggggatga cgtcaagtcc tcatggccct tatgggtagg gcttcacacg   1200
tcatacaatg gtcggaacag agggtcgcta agccgcgagg tggagccaat cccagaaaac   1260
cgatcgtagt ccggatcgta gtctgcacct cgactacgtg aagctggaat cgctagtaat   1320
cgcggatcag catgccgcgg tgaatacgtt cccgggtctt gtacacaccg cccgtcacac   1380
catgggagtg ggttttacca gaagtggcta gtctaaccgc aa                     1422
```

BURKHOLDERIA AND APPLICATIONS THEREOF

CROSS REFERENCE TO RELATED APPLICATIONS

This application is the national phase entry of International Application No. PCT/CN2017/107682, filed on Oct. 25, 2017, which is based upon and claims priority to Chinese Patent Application No. 201710857192.1, filed on Sep. 20, 2017, the entire contents of which are incorporated herein by reference.

TECHNICAL FIELD

The present invention relates to a strain of *Burkholderia* and the method for using it in the asymmetrical oxidation of thioethers to synthesize chiral sulfoxides.

BACKGROUND 5-methoxy-2-((S)-((4-methoxy-3,5-dimethyl-2-pyridyl) methyl)sulfinyl)-1H-benzimidazole sodium may be used for treating duodenal ulcer, gastric ulcer, gastritis and gastrointestinal esophagitis. Significant advances have been made in chemical processes which utilize metals and small molecule organic catalysts to oxidize the thioether asymmetrically for synthesis. However, there are disadvantages in such processes, such as over oxidation, more by-products, complex separation and purification process.

A biological process was used for performing an asymmetrical oxidation on thioether compounds to give the chiral sulfoxide with a single enantiomer, which process has little pollution to environment, less by-products, a good atom economy, and a high optical purity of the products. Therefore, it has received more focus on the biological process of an asymmetrical oxidation to synthesize the chiral sulfoxide.

U.S. Pat. No. 5,840,552 disclosed a method for preparing 5-methoxy-2-(-((4-methoxy-3,5-dimethyl-2-pyridyl) methyl)sulfinyl)-1H-benzimidazole single enantiomer by selectively oxidizing a prochiral thioether with a microorganism, but the activity of which was very low and the product concentration was at ppm level; and the disclosed *Penicillin frequentans, Rhizopusstolonifer, Ustilagomaydis, Arthrobacter petroleophagus, Breyibacterium paraffinolyticum, Mycobacterium* sp., *Acinetobacter* sp. all catalyze the oxidation of thioether to generate 5-methoxy-2-((R)-((4-methoxy-3,5-dimethyl-2-pyridyl)methyl)sulfinyl)-1H-benzimidazole, not the desired 5-methoxy-2-((S)-((4-methoxy-3,5-dimethyl-2-pyridyl)methyl)sulfinyl)-1H-benzimidazole. Inventors have already screened and obtained a strain of *Rhodococcus* sp. (CGMCC NO. 2547) which may catalyze the asymmetrical oxidation of a series of prochiral phenyl-alkyl thioethers and derivatives thereof, obtaining the optically active chiral phenyl methyl sulfoxide and derivatives thereof (CN101372676A). Czech scientists have screened and obtained a strain of *Lysinibacillus* sp., which utilized its growth cells to catalyze thioether to generate 5-methoxy-2-((S)-((4-methoxy-3,5-dimethyl-2-pyridyl)methyl)sulfinyl)-1H-benzimidazole, but when the concentration of substrate was 0.1 g/L, the conversion rate at 44 h was only 43% (*Bioresources Technology* 2011, 102:7621-7626). Patent CN106191193A disclosed a method for preparing 5-methoxy-2-((S)-((4-methoxy-3,5-dimethyl-2-pyridyl) methyl)sulfinyl)-1H-benzimidazole through the asymmetrical oxidation with immobilized *Aspergillus niger*, while the cell culture time exceeded 72 h, and the addition amount of cells was too large, and the immobilization process was complex, which all increase the preparation cost of catalysts.

To overcome the limitation of the prior art, the present invention has designed a screening strategy again, which screens new microorganism strains from the soil natural treasury, providing a new resource of biocatalysts.

SUMMARY

In the present invention, soil samples were extensively collected from soils with different properties, and cultured in thioether substrates with different gradient of concentrations. The strains in the soil were enriched and acclimated, and screened to give a batch of bacteria capable of catalyzing the asymmetrical oxidation of thioether.

The first aspect of the present invention disclosed a strain of *Burkholderia*, named *Burkholderia glathei* ECU0712. The strain was preserved in the China General Microbiological Culture Collection Center (CGMCC) on Jul. 26, 2017, the preservation address is No. 3 Yard 1, Beichen West Road, Chaoyang District, Beijing, with an accession number of CGMCC NO. 14464.

*Burkholderia glathei* ECU0712 of the present invention has the following morphological characteristics: Gram-negative bacterium, no sporulation, rod, width of 0.6-0.9 μm, length of 1.1-1.4 μm. The colony is round, white, humid, translucent, with regular margin.

Biological classification is the denomination and grading on various biological groups following the principles and methods of taxonomy. Classification was generally made in terms of kingdoms, phylums, classes, orders, families, genera, and species; in which species are the basic taxonomic unit. In biology, binominal nomenclature is commonly used for the naming of organisms; that is, the name of each species is composed of two parts, generic name plus specific epithet (specific name); in the printed publication of scientific literatures, expressions in italic are generally used.

Nomination of specific strains may be in a manner of generic name+specific name+strain code, e.g., *Burkholderia glathei* ECU0712. *Burkholderia* indicates the generic name, *glathei* indicates the specific name, ECU0712 indicates the strain code. *Burkholderia* can be translated as *Burkholderia* sp., also as *Burkholderia*, *glathei* can be translated as *glathei*. There has been found more than 38 species in *Burkholderia* sp., the most common of which is *Burkholderia cepacia*.

*Burkholderia glathei* ECU0712 disclosed in the present invention may be in various viable states, for example growth cell state, resting cell state, or lyophilized cell state. The resting cell is also known as non-growing cell, which is in dormant state, without growth and reproduction, capable of restoring the growth in an appropriate condition.

Exemplarily, resting cells could be obtained by cultivating the *Burkholderia glathei* ECU0712 and centrifuging the cultured mixture. The acquisition of resting cells through centrifugation is the conventional method to persons skilled in the art; for example the centrifugal rotational speed is 8000-10000 rpm, the time is 15-30 min.

Exemplarily, the *Burkholderia glathei* ECU0712 lyophilized cells could be obtained by employing the freeze drying technology conventional in the art (e.g., the refrigerator pre-freezing temperature of −80° C. conventional in the lab; the vacuum degree at 0.1-0.2 mbar, temperature of −50° C.--80° C., freeze drying for 24-48 h) on the *Burkholderia glathei* ECU0712 resting cells. The lyophilized cells may be stored at 4° C. ready for use.

The present invention also disclosed a method for cultivating the *Burkholderia glathei*; the *Burkholderia glathei* was preferably the *Burkholderia glathei* ECU0712. It may be fermental cultivated by conventional cultivation methods, such as shake-flask cultivation, fermentor cultivation or the like. Exemplary composition of the fermentation medium is: 2.0-10.0 g/L peptone, 2.0-10.0 g/L yeast extract, 2.0-10.0 g/L sodium chloride, pH 5.0-8.0.

The second aspect of the present invention disclosed the *Burkholderia glathei* extract. The *Burkholderia glathei* preferably is *Burkholderia glathei* ECU0712.

The *Burkholderia glathei* extract disclosed in the present invention includes a cell free extract, or the lyophilized product of the cell free extract. The cell free extract is obtained by crushing and separating the cells; common separation means include, but not limited to, centrifugation. Exemplarily, cells are suspended in a buffer, filtered, crushed (include, but not limited to, ultrasonication, 800-1000 bar high-pressure disruption), the supernatant collected by centrifugation, to give the cell free extract; the rotational speed of centrifugation may be 14000-18000 rpm, the time may be 20-30 min.

The lyophilized product of the cell free extract could be obtained by freeze drying the cell free extract. Exemplarily, the lyophilized product of the cell free extract could be obtained by pre-freezing the cell free extract (e.g., using the refrigerator at −80° C. conventional in the lab) with the conventional freeze drying technology (e.g., the vacuum degree at 0.1-0.2 mbar, temperature of −50° C.--80° C., freeze drying for 24-48 h). The lyophilized product of the cell free extract may be stored at 4° C. ready for use.

It can be known by persons skilled in the art that, the cell free extract, or the lyophilized product of the cell free extract described in the present invention include a variety of proteinaceous materials and others. Of those, what are capable of catalyzing the asymmetrical oxidation of thioether substrates are proteinaceous materials (generally enzymes) with chiral sulfoxide functions, the kinds of which are unidentified, and the contents of which are generally minor; and could not be ascertained and determined through simple works.

The *Burkholderia glathei* extract described in the present invention may be further immobilized. Upon the immobilization, the *Burkholderia glathei* extract could be used repeatedly and consecutively. The catalytic reaction described in the present inventions is generally carried out in an aqueous solution (that may contain a certain amount of organic solvent), while immobilization is to treat the *Burkholderia glathei* extract with a physical or chemical process to make it nonsoluble in water, while still in a state of catalytic activity. Exemplarily, the cell free extract (for example, its lyophilized product) is immobilized with polyethyleneimine (PEI) by a chemical process with glutaraldehyde as the crosslinking agent.

The third aspect of the present invention discloses the use of the *Burkholderia glathei* or its extract in catalyzing the asymmetrical oxidation of thioethers to chiral sulfoxides; the *Burkholderia glathei* preferably is *Burkholderia glathei* ECU0712.

Thioether is a class of compounds with the general formula of $R_A$—S—$R_B$; wherein $R_A$, $R_B$ may be the same or different. With respect to industrial applications, the thioether of the present invention is preferably selected from the following compounds or pharmaceutically acceptable salts thereof:

Formula I

Compound OME, in formula I, $R_1$=CH$_3$O—, $R_2$=CH$_3$—, $R_3$=CH$_3$O—, $R_4$=CH$_3$—;

Compound LAN, in formula I, $R_1$=H, $R_2$=CH$_3$—, $R_3$=CF$_3$CH$_2$O—, $R_4$=H;

Compound PAN, in formula I, $R_1$=F$_2$CHO—, $R_2$=CH$_3$O—, $R_3$=CH$_3$O—, $R_4$=H;

Compound RAB, in formula I, $R_1$=H, $R_2$=CH$_3$—, $R_3$=CH$_3$—O—CH$_2$—CH$_2$—CH$_2$O—, $R_4$=H;

Compound ILA, in formula I, $R_1$ = (pyrrolyl), $R_2$=CH$_3$—, $R_3$=CH$_3$O—, $R_4$=H.

When thioether is compound OME or a pharmaceutically acceptable salt thereof, the chiral sulfoxide obtained from the asymmetrical oxidation of thioether is 5-methoxy-2-((S)-((4-methoxy-3,5-dimethyl-2-pyridyl)methyl)sulfinyl)-1H-benzimidazole or a pharmaceutically acceptable salt thereof; as shown in formula II.

Formula II

When thioether is compound PAN or a pharmaceutically acceptable salt thereof, the chiral sulfoxide obtained from the asymmetrical oxidation of thioether is 5-difluoromethoxy-2-[[(S)-(3,4-dimethoxy-2-pyridyl)-methyl]sulfinyl]-1H-benzimidazole or a pharmaceutically acceptable salt thereof; as shown in formula III.

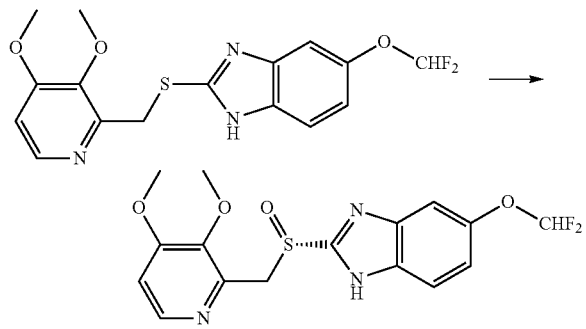

Formula III

When thioether is compound ILA or a pharmaceutically acceptable salt thereof, the chiral sulfoxide obtained from the asymmetrical oxidation of thioether is 5-(1H-pyrrol-1-yl)-2-[(R)-[(4-methoxy-3-methyl-2-pyridyl)-methyl]sulfinyl]-1H-benzimidazole or a pharmaceutically acceptable salt thereof; as shown in formula IV.

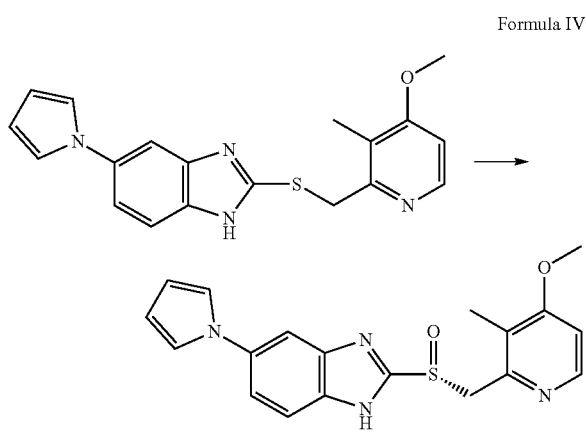

Formula IV

The fourth aspect of the present invention discloses a method for using the *Burkholderia glathei* or its extract on catalyzing the asymmetrical oxidation of thioethers to chiral sulfoxides; the *Burkholderia glathei* preferably is *Burkholderia glathei* ECU0712.

The method is adding the *Burkholderia glathei* or its extract into an appropriate reaction system together with thioether to give the reaction target products.

The reaction is carried out in a buffer solution. With regard to the pH of the buffer solution, it is preferably pH=7.5-9.0, further preferably is pH=8.0-9.0, and further preferably is pH=8.5-9.0. With regard to the composition of the buffer solution, it is preferably selected from a sodium phosphate buffer, a Tris-HCl buffer, a glycine-sodium hydroxide buffer, or a potassium phosphate buffer solution; further preferably is a potassium phosphate buffer solution;

The reaction temperature preferably is 15-35° C., further preferably is 20-35° C., further preferably is 20-30° C., yet most preferably is 25-30° C.

The reaction time preferably is 4-48 hours, further preferably is 5-48 hours; further preferably is 6-48 hours; yet further preferably is 7-48 hours; yet most preferably is 8-48 hours. The longer reaction time is feasible from a technology perspective, while from an industrial perspective, a more economical reaction time period will be chosen, so the reaction time may preferably be 8-16 hours.

The concentration of thioether in the reaction system preferably is 1-100 g/L, further preferably is 1-20 g/L.

The thioether preferably is dissolved in a cosolvent, the cosolvent is a water soluble organic solvent. The cosolvent preferably is selected from one or more of acetonitrile, tert-butanol, tetrahydrofuran, ethanol, isopropanol, N-methylpyrrolidone, dimethylsulfoxide, methanol, acetone, dimethylformamide; further preferably is selected from one or more of ethanol, isopropanol, N-methylpyrrolidone, dimethylsulfoxide, methanol, acetone, dimethylformamide; more further preferably is selected from one or more of dimethylsulfoxide, methanol, acetone, dimethylformamide.

Preferably, the cosolvent makes up 2-15% the volume of the reaction system, further preferably, the cosolvent makes up 5-10% the volume of the reaction system.

With regard to the products obtained from the reaction, they may be extracted with solvents such as dichloromethane, ethyl acetate or the like at the end of the reaction, and then centrifugated, the organic phase was taken and the organic solvent was evaporated off to give the product.

Exemplary qualitative and quantitative analysis methods for the substrates, products, by-products of the asymmetrical oxidation of thioether may be those disclosed in Embodiment 7 of the present invention.

When thioether is compound OME or a pharmaceutically acceptable salt thereof, the chiral sulfoxide obtained from the asymmetrical oxidation of thioether is 5-methoxy-2-((S)-((4-methoxy-3,5-dimethyl-2-pyridyl)methyl)sulfinyl)-1H-benzimidazole or a pharmaceutically acceptable salt thereof. It was demonstrated from exemplary research that, for the product 5-methoxy-2-((S)-((4-methoxy-3,5-dimethyl-2-pyridyl)methyl)sulfinyl)-1H-benzimidazole, the yield ratio is greater than 90%, ee value is greater than 99%, the proportion of the by-product sulfone is lower than 0.1%.

*Burkholderia glathei* or its extract disclosed in the present invention, preferably *Burkholderia glathei* ECU0712 or its extract, has significant advantages in terms of catalyzing the asymmetrical oxidation of thioether to a chiral sulfoxide, with a high product yield, a high product optical purity (greater than 99%), and a low by-product content; and benefits such as a simple reaction system and a short preparation time for the catalysts.

DETAILED DESCRIPTION OF THE EMBODIMENTS

Figure 1:
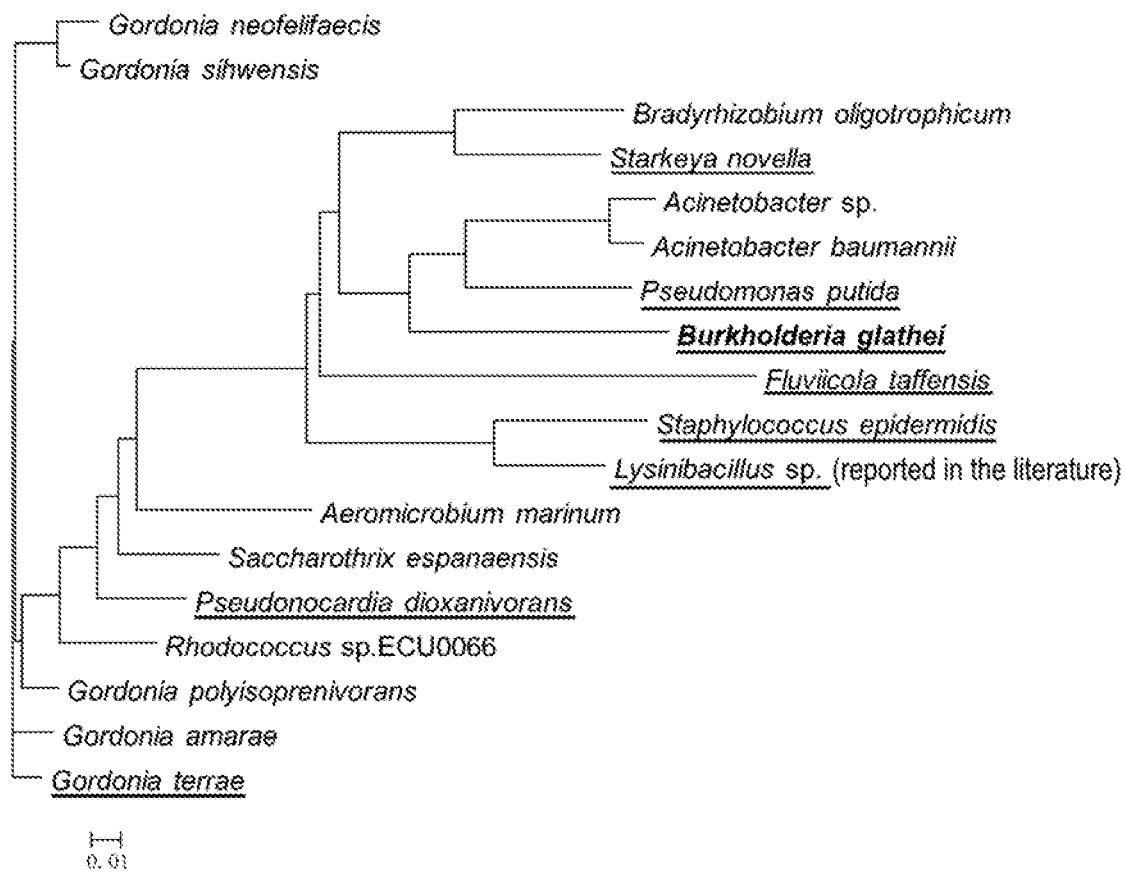
FIG. 1: The phylogenetic tree of species of strains obtained from the screening of Embodiment 1 which were capable of asymmetrically oxidizing the compound OME; wherein *Lysinibacillus* sp. is the strain reported in the prior art which was capable of asymmetrically oxidizing the compound OME; in this figure, the underlined strain indicated that the product of asymmetrical oxidation was 5-methoxy-2-((S)-((4-methoxy-3,5-dimethyl-2-pyridyl)methyl)sulfinyl)-1H-benzimidazole.

Embodiment 1. Screening of Strains (1) 252 soil samples from different environments were harvested, including Shanghai Fengxian Chemical District, Xinhua Hospital, the Vicinity of Orchard and River, Greenbelts, Schoolyard, Residential Greening, Shanghai Botanical Garden, etc. The screening process employed four cycles of enrichment culture, the preliminary poor medium formulation was yeast powder 2 g/L, $(NH_4)_2SO_4$ 1.0 g/L, $K_2HPO_4 \cdot 3H_2O$ 6.0 g/L, $KH_2PO_4$ 3.0 g/L, NaCl 0.5 g/L, $MgSO_4 \cdot 7H_2O$ 0.5 g/L, $CaCl_2$) 0.05 g/L, pH 7.0, the concentration of yeast powder in each cycle of passage enrichment culture was reduced by half, while the concentration of the substrate (compound OME) (the first-run concentration was 0.1 mM) doubled in each cycle of cultivation, upon screening, to obtain the target strains capable of using the substrate as the carbon source and transforming the substrate. After culturing for 1-2 days, soil sample tubes in which the culture solution was cloudy and the bacteria grew well were chosen, from which was sucked up 500 µL bacteria solution, into which was added 4 mL fresh poor medium, and then the next cycle of enrichment was started. Upon the completion of four cycles of enrichment culture, they were analyzed by thin-layer chromatography, samples with the substrate significantly reduced were isolated using plate streaking, and single colonies were selected.

(2) Single colonies were inoculated into 10 ml rich medium (glucose 1.5 g/L, peptone 0.5 g/L, yeast powder 0.5 g/L, $Na_2HPO_4 \cdot 2H_2O$ 0.05 g/L, $NaH_2PO_4$ 0.05 g/L, NaCl 1.0 g/L, $MgSO_4$ 0.05 g/L), cultivated at 30° C. for 24 h and then the bacteria was harvested by centrifugation, into which was added 1 mL potassium phosphate buffer (100 mM, pH 9.0), and the substrate (compound OME, DMSO cosolvent, the final concentration 1.0 mM) was added to react. The reaction was stopped after 24 h, and extracted with 700 µL ethyl acetate, the extract was dried and then the conversion ratio was determined by the high-performance liquid chromatography, in which the strains with the conversion ratio greater than 1% were selected for second-screening.

(3) Single colonies were inoculated into 100 ml of the above rich medium, cultivated at 30° C. for 24 h and then the bacteria was harvested by centrifugation, into which was added 5 mL potassium phosphate buffer (KPB, pH 9.0), and the substrate (compound OME, DMSO cosolvent, the final concentration 1.0 mM) was added to react. The reaction was stopped after 24 h, and a sample of 1 ml was taken and extracted with 700 µL ethyl acetate, the extract was dried and then the optical purity of the product was analyzed with a chiral column.

(4) Upon repeated comparisons, a batch of bacteria capable of oxidizing compound OME were screened and obtained, including 7 strains which may oxidize compound OME to produce 5-methoxy-2-((S)-((4-methoxy-3,5-dimethyl-2-pyridyl)methyl)sulfinyl)-1H-benzimidazole, 10 strains which may oxidize thioether to produce 5-methoxy-2-((R)-((4-methoxy-3,5-dimethyl-2-pyridyl)methyl)sulfinyl)-1H-benzimidazole. The phylogenetic tree of these microorganism species was drawn according to 16S rDNA, as shown in FIG. 1, from which it was found that there were great differences between the *Burkholderia glathei* obtained by screening and the *Lysinibacillus* sp. reported in the literatures. The optical purity results of the products of the catalytic oxidation of compound OME by these microorganisms were shown in Table 1.

TABLE 1

Screening results of compound OME oxidation strains

| Strain | ee (%) |
| --- | --- |
| *Gordonia neofelifaecis* | 99.9 (R) |
| *Bradyrhizobium oligotrophicum* | 99.9 (R) |

TABLE 1-continued

Screening results of compound OME oxidation strains

| Strain | ee (%) |
| --- | --- |
| *Aeromicrobium marium* | 99.9 (R) |
| *Gordonia polyisoprenivorans* | 90.6 (R) |
| *Gordonia amarae* | 90.3 (R) |
| *Rhodococcus* sp. ECU0066 | 80.2 (R) |
| *Gordonia sihwensis* | 79.5 (R) |
| *Saccharothrix espanaensis* | 70.5 (R) |
| *Acinetobacter* sp. | 67.4 (R) |
| *Acinetobacter baumannii* | 66.6 (R) |
| *Burkholderia glathei* | 99.1 (S) |
| *Pseudomonas putita* | 87.2 (S) |
| *Gordonia terrae* | 86.8 (S) |
| *Staphylococcus epidermidis* | 85.1 (S) |
| *Pseudonocardia dioxanivorans* | 83.4 (S) |
| *Starkeya novella* | 81.8 (S) |
| *Fluviicola taffensis* | 76.1 (S) |

Embodiment 2. Identification of *Burkholderia glathei* ECU0712

(1) Genomic DNA of strains was extracted by general methods, and PCR amplification was carried out using 16S rDNA amplification universal primers, with the genomic DNA of strains as the template. After detection by agarose gel electrophoresis, target fragments of about 1400 bp were amplified. PCR products were purified and recycled with gel purification kits (Agarose Gel DNA Extraction Kit from Beijing Tiangen Biochemical Co.). Finally, the recycled DNA fragments were sequenced, with the sequencing results shown in SEQ ID No. 1.

(2) 16S rDNA sequence was aligned in NCBI database. The 16S rDNA similarity between the strain obtained and *Burkholderia glathei* (also named *Caballeronia glathei*) was 99%, so the strain we obtained was named as *Burkholderia glathei* ECU0712.

(3) *Burkholderia glathei* ECU0712 described in the present invention has the following morphological characteristics: Gram-negative bacterium, no sporulation, rod, width of 0.6-0.9 µm, length of 1.1-1.4 µm. The colony is round, white, humid, translucent, with regular margin.

Embodiment 3. Shake-Flask Cultivation of *Burkholderia glathei* ECU0712

Inclined bacterial strains preserved at 4° C. were taken and inoculated into the LB fermentation medium in a tube (peptone 10 g/L, yeast extract 5 g/L, sodium chloride 10 g/L, pH 7.2), cultivated with shaking at 200 rpm for 10 h at 30° C., forming the seed solution. 2 ml seed solution was inoculated into 100 ml fermentation medium (5 g/L peptone, 5.0 g/L yeast extract, 5.0 g/L sodium chloride, pH 6.5) with a proportion of 2%, cultivated for 24 h at 30° C., centrifugated, and washed to give the resting cells.

Embodiment 4. Fermentor Cultivation of *Burkholderia glathei* ECU0712

Inclined bacterial strains preserved at 4° C. were taken and inoculated into the LB fermentation medium in a tube (peptone 10 g/L, yeast extract 5 g/L, sodium chloride 10 g/L, pH 7.2), cultivated with shaking at 200 rpm for 10 h at 30° C., forming the seed solution. 300 ml seed solution was inoculated into a 5 L fermentor charged with 3 L fermentation medium (10.0 g/L peptone, 5.0 g/L yeast extract, 8.0 g/L sodium chloride, pH7.0), cultivated for 18 h at 30° C., and then centrifugated, and washed to give the resting cells which were ready for being used in the preparation reactions.

Embodiment 5. Preparation of *Burkholderia glathei* ECU0712 Lyophilized Cells Cells obtained from Embodiment 4 were first placed into a −80° C. refrigerator to prefreeze overnight, freeze dried for 24 h at the conditions of 0.1-0.2 mbar vacuum degree and −65° C. freezing temperature, to give the lyophilized cells, which can be stored at 4° C. ready for use.

Embodiment 6. Preparation of *Burkholderia glathei* ECU0712 Cell Free Extract and the Lyophilized Products of the Cell Free Extract Cells obtained from Embodiment 4 were resuspended with 1 L potassium phosphate buffer (10 mM, pH 7.0), the suspension was filtered through a 100-mesh sieve and then crushed consecutively at a pressure of 1000 bar for two times. The centrifugal speed of the crushed solution was 15000 rpm, and the centrifuge time was 30 min. The crushed supernatant was collected to give the cell free extract.

The crushed supernatant was placed into a −80° C. refrigerator to prefreeze overnight, freeze dried for 48 h at the conditions of 0.1-0.2 mbar vacuum degree and −65° C. freezing temperature, to give the lyophilized products of the cell free extract, which can be stored at 4° C. ready for use.

Embodiment 7. Qualitative and Quantitative Analysis on the Substrates, Products, by-Products (1) Silica gel thin layer chromatography was employed as the qualitative analysis method for detecting whether there were products generated or not. Capillaries fed with extracted samples were dotted on a GF silica gel plate, placed in a developing bottle, in which the developer composition was ethyl acetate volume:ether volume=10:1, taken out when the leading edge of the solvent was apart from the top of the plate at 1 cm. The volatilization of the solvent was accelerated using a blower. Upon the volatilization of the solvent, it was observed by an ultraviolet analyzer and compared with a standard sample. Rf of the substrate (compound OME)=0.1, Rf of the product 5-methoxy-2-(-((4-methoxy-3,5-dimethyl-2-pyridyl)methyl)sulfinyl)-1H-benzimidazole=0.42.

(2) Determination of the conversion ratio by a reversed-phase high-performance liquid chromatography: The conversion ratio of the substrate (compound OME) being converted to the product 5-methoxy-2-(-((4-methoxy-3,5-dimethyl-2-pyridyl)methyl)sulfinyl)-1H-benzimidazole was detected using a water phase chromatography HPLC, and the substrate and product were quantitatively analyzed. A $C_{18}$ reversed-phase column (Elite Hypersil BDS $C_{18}$, 5 µm, 4.6 mm×250 mm) was employed, the mobile phase was acetonitrile:water=53:47 (volume), with a flow rate of 1 ml·min$^{-1}$, the column temperature at 30° C., the feed amount at 10 µl, the detecting wavelength at 250 nm, the retention time of the product and the substrate was 3.9 min (the mixture of R configuration and S configuration) and 5.7 min, respectively.

(3) Determination of the optical purity of the product and the proportion of the by-product using normal phase high-performance liquid chromatography: AS-H column was employed to analyze the optical purity of the product, the mobile phase was n-hexane:isopropanol=30:70 (volume), with a flow rate of 0.5 ml/min, the column temperature at 30° C. the feed amount at 10 µl, the detecting wavelength at 250 nm, the retention time of the substrate, sulfoxide in R-configuration, the product in S-configuration, and the by-product sulphone was about 8.3 min, 12.2 min, 15.3 min and 9.3 min, respectively.

Embodiment 8. pH Optimization of Oxidation of Compound OME

To a 1 ml reaction system was added the substrate (compound OME) 1 g/L (solubilized with DMSO, 10% v/v; indicating that the substrate concentration in the reaction system was 1 g/L, the substrate was added into the reaction system after being solubilized with DMSO amounting 10% of the reaction system), the resting cells described in Embodiment 3, 1 g/L, glucose 1 g/L. The pH of the reaction was controlled with a potassium phosphate buffer (50 mM, pH 7.5, 8.0, 8.5 or 9.0). The reaction was carried out at 20° C. for 8 h, then samples were taken to analyze the conversion ratio of the reaction, as shown in Table 2.

TABLE 2 pH Optimization of Oxidation of Compound OME

| No. | pH of the Reaction | Conversion Ratio (%) |
|---|---|---|
| 1 | 7.5 | 78 |
| 2 | 8.0 | 88 |
| 3 | 8.5 | 100 |
| 4 | 9.0 | 96 |

Embodiment 9. Temperature Optimization of Oxidation of Compound OME

To a 1 ml reaction system was added the substrate (compound OME) 2 g/L (solubilized with acetone, 5% v/v), the resting cells described in Embodiment 3, 1 g/L, glucose 1 g/L. The pH of the reaction was controlled with a potassium phosphate buffer (50 mM, pH 8.5). The reaction was carried out at different temperatures for 12 h, then samples were taken to analyze the conversion ratio of the reaction and the proportion of the by-products, as shown in Table 3.

TABLE 3

Temperature Optimization of Oxidation of Compound OME

| No. | Reaction Temperature | Conversion Ratio (%) | Proportion of By-products (%) |
|---|---|---|---|
| 1 | 15 | 45 | 0 |
| 2 | 20 | 70 | 0 |
| 3 | 25 | >99 | 0.1 |
| 4 | 30 | >99 | 1.1 |
| 5 | 35 | >99 | 8.5 |

Embodiment 10. Cosolvent Optimization of Oxidation of Compound OME

To a 10 ml reaction system was added the substrate (compound OME) 5 g/L (solubilized with different cosolvents, 5% v/v), the lyophilized yeast powder 2 g/L, glucose 5 g/L, NADP$^+$ 0.2 mM. The pH of the reaction was controlled with a potassium phosphate buffer (50 mM, pH 8.5). The reaction was carried out at 25° C. for 12 h, then samples were taken to analyze the conversion ratio of the reaction, as shown in Table 4. Wherein: "+" represents a conversion ratio of 1-10%, "++" represents a conversion ratio of 10.1-30%, "+++" represents a conversion ratio of 30.1-60%, "++++" represents a conversion ratio of 60.1-100%.

TABLE 4

Cosolvent Optimization of Oxidation of Compound OME

| No. | Cosolvent | Conversion Ratio of the Reaction |
|---|---|---|
| 1 | blank | + |
| 2 | dimethylsulfoxide | ++++ |
| 3 | methanol | ++++ |
| 4 | ethanol | +++ |
| 5 | acetonitrile | ++ |
| 6 | acetone | ++++ |
| 7 | tert-butanol | ++ |
| 8 | isopropanol | +++ |
| 9 | dimethylformamide | ++++ |
| 10 | tetrahydrofuran | ++ |
| 11 | N-methylpyrrolidone | +++ |

Figure 2:
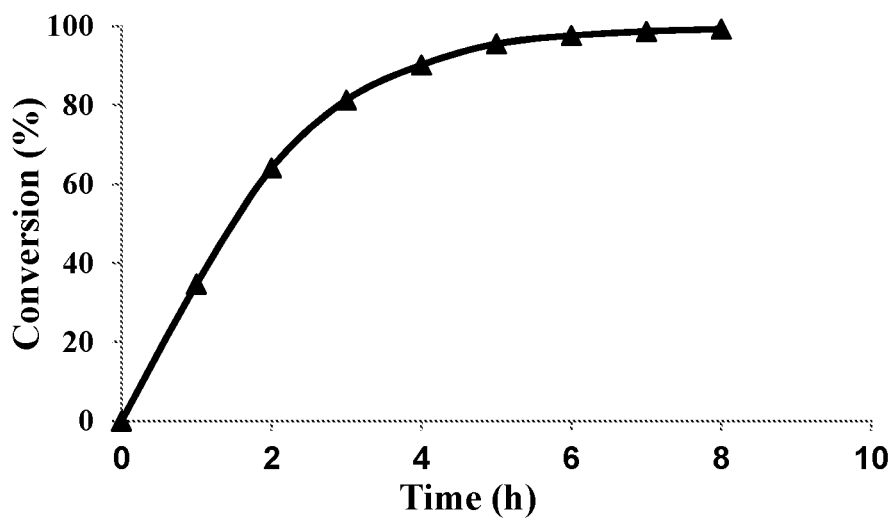
FIG. 2: Process curve of immobilized *Burkholderia glathei* ECU0712 extract for catalyzing the oxidation of the compound OME.

Embodiment 11. Immobilization and Catalytic Reactions of the *Burkholderia glathei* ECU0712 Extract The lyophilized product of the cell free extract prepared in Embodiment 6 has been immobilized by means of crosslinked enzyme aggregates. Polyethyleneimine (PEI) was chosen as the preferable enzyme sediment reagent, the best mass ratio between PEI and the lyophilized product of the cell free extract was 2:1; glutaraldehyde was chosen as the crosslinking agent for the sedimentation of aggregates, the most suitable concentration was 0.2% (w/v). The prepared aggregates suspension was suction filtered, and the resulting filter cake was washed repeatedly with KPB (100 mM, pH 7.0), with the residual glutaraldehyde being washed off, to obtain the immobilized *Burkholderia glathei* extract useful for the oxidation of compound OME. To a 100 ml reaction system were added the substrate (compound OME) 10 g/L (solubilized with DSMO, 5% v/v), the immobilized *Burkholderia glathei* extract 5 g/L, glucose 5 g/L, NADP$^+$ 0.2 mM. The pH of the reaction was controlled with a potassium phosphate buffer (50 mM, pH 8.5). The reaction was carried out at 25° C. for different times, then samples were taken to detect the progress of the reaction, as shown in FIG. 2, the conversion ratio of reaction when reacted for 4 hours may be greater than 90%, the conversion ratio of reaction when reacted for 5 hours may be greater than 95%, and the conversion ratio of reaction when reacted for 8 hours may be greater than 99%.

Figure 3:
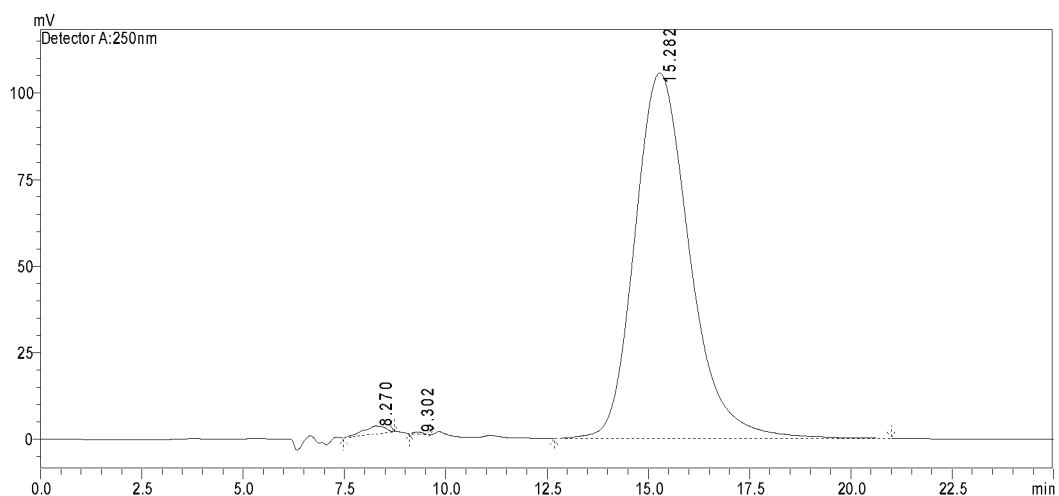
FIG. 3: Liquid chromatograph spectrum of the product obtained from Embodiment 12.

Embodiment 12. Preparation of 5-methoxy-2-((S)-((4-methoxy-3,5-dimethyl-2-pyridyl)methyl)sulfinyl)-1H-benzimidazole To a 1 L reaction system were added the substrate (compound OME) 20 g/L (solubilized with DSMO, 10% v/v), the lyophilized cells prepared in Embodiment 5 15 g/L, glucose 10 g/L, NADP$^+$ 0.2 mM. The pH of the reaction was controlled with a potassium phosphate buffer (50 mM, pH 8.5), and the reaction was carried out at 25° C. for 16 h. After completion, the reaction was extracted with dichloromethane and then centrifugated, the organic phase was taken and dichloromethane was evaporated off to give the product 5-methoxy-2-((S)-((4-methoxy-3,5-dimethyl-2-pyridyl)methyl)sulfinyl)-1H-benzimidazole 19.36 g, with a yield of 92.32%, the ee value of the product being greater than 99%, the proportion of the by-product sulphone being lower than 0.1%, with the liquid phase chromatogram as shown in FIG. 3.

Embodiment 13. Oxidation of Compound PAN

To a 1 L reaction system were added the substrate (compound PAN) 5 g/L (solubilized with DSMO, 10% v/v), the lyophilized cells prepared in Embodiment 5 15 g/L, glucose 10 g/L, NADP$^+$ 0.2 mM. The pH of the reaction was controlled with a potassium phosphate buffer (50 mM, pH 8.5), and the reaction was carried out at 25° C. for 10 h. After completion, the reaction was extracted with dichloromethane and then centrifugated, the organic phase was taken and dichloromethane was evaporated off to give the product 4.53 g, with a yield of 86.78%, the ee value of the product being greater than 99%. The product was 5-difluoromethoxy-2-[[(S)-(3,4-dimethoxy-2-pyridyl)-methyl]sulfinyl]-1H-benzimidazole.

Embodiment 14. Oxidation of Compound ILA

To a 1 L reaction system were added the substrate (compound ILA) 5 g/L (solubilized with DSMO, 10% v/v), the lyophilized cells prepared in Embodiment 5 15 g/L, glucose 10 g/L, NADP$^+$ 0.2 mM. The pH of the reaction was controlled with a potassium phosphate buffer (50 mM, pH 8.5), and the reaction was carried out at 25° C. for 10 h. After completion, the reaction was extracted with dichloromethane and then centrifugated, the organic phase was taken and dichloromethane was evaporated off to give the product 2.33 g, with a yield of 44.64%, the ee value of the product being greater than 99%. The product was 5-(1H-pyrrol-1-yl)-2-[(R)-[(4-methoxy-3-methyl-2-pyridyl)-methyl]sulfinyl]-1H-benzimidazole.

What is claimed is:

1. An immobilized *Burkholderia glathei* extract from the, wherein, the *Burkholderia glathei* is *Burkholderia glathei* ECU0712, preserved in the China General Microbiological Culture Collection Center, with an accession number of CGMCC NO. 14464;

the immobilized *Burkholderia glathei* extract is prepared by immobilizing a cell free extract, or a lyophilized product of the cell free extract of *Burkholderia glathei* ECU0712; the cell free extract is obtained by crushing and separating the *Burkholderia glathei*; and the immobilizing is performed with a physical process or a chemical process to make the cell free extract or the lyophilized product of the cell free extract nonsoluble in water, while still in a state of catalytic activity.

2. The immobilized *Burkholderia glathei* extract of claim 1, wherein, the cell free extract or the lyophilized product of the cell free extract is immobilized with polyethyleneimine (PEI) by a chemical process with glutaraldehyde as a crosslinking agent.

3. A method of preparing a chiral sulfoxide by an asymmetrical oxidation of a thioether, comprising a step of using an immobilized extract of the *Burkholderia glathei* as a catalyst for catalyzing the asymmetrical oxidation of the thioether to the chiral sulfoxide, wherein the *Burkholderia glathei* has an accession number of CGMCC NO. 14464, the extract is a cell free extract, or a lyophilized product of the cell free extract; and the cell free extract k obtained by crushing and separating the *Burkholderia glathei*.

4. The method of claim 3, wherein, the extract of the *Burkholderia glathei* is immobilized in polyethyleneimine with glutaraldehyde as a crosslinking agent.

5. The method of claim 4, wherein, the thioether is selected from the following compounds or pharmaceutically acceptable salts of the following compounds:

formula I a first compound, having the structure of the formula I, wherein $R_1$ is $CH_3O$—, $R_2$ is $CH_3$—, $R_3$ is $CH_3O$—, and $R_4$ is $CH_3$—;

a second compound, having the structure of the formula I, wherein $R_1$ is H, $R_2$ is $CH_3$—, $R_3$ is $CF_3CH_2O$—, and $R_4$ is H;

a third compound, having the structure of the formula I, wherein $R_1$ is $F_2CHO-$, $R_2$ is $CH_3O-$, $R_3$ is $CH_3O-$, and $R_4$ is H;

a fourth compound, having the structure of the formula I, $R_1$ is H, $R_2$ is $CH_3-$, $R_3$ is $CH_3-O-CH_2-CH_2-CH_2O-$, and $R_4$ is H; and a fifth compound, having the structure of the formula I, $R_1$ is

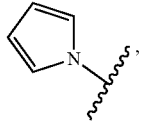

$R_2$ is $CH_3-$, $R_3$ is $CH_3O-$, and $R_4$ is H.

6. The method of claim 5, wherein:

when the thioether is the first compound or a pharmaceutically acceptable salt of the first compound, the chiral sulfoxide is 5-methoxy-2-((S)-((4-methoxy-3,5-dimethyl-2-pyridyl)methyl)sulfinyl)-1H-benzimidazole or a pharmaceutically acceptable salt of 5-methoxy-2-((S)-((4-methoxy-3,5-dimethyl-2-pyridyl)methyl)sulfinyl)-1H-benzimidazole;

when the thioether is the third compound or a pharmaceutically acceptable salt of the third compound, the chiral sulfoxide is 5-difluoromethoxy-2-[[(S)-(3,4-dimethoxy-2-pyridyl)-methyl]sulfinyl]-1H-benzimidazole or a pharmaceutically acceptable salt of 5-difluoromethoxy-2-[[(S)-(3,4-dimethoxy-2-pyridyl)-methyl]sulfinyl]-1H-benzimidazole;

when the thioether is the fifth compound or a pharmaceutically acceptable salt of the fifth compound, the chiral sulfoxide is 5-(1H-pyrrol-1-yl)-2-[(R)-[(4-methoxy-3-methyl-2-pyridyl)-methyl]sulfinyl]-1H-benzimidazole or a pharmaceutically acceptable salt of 5-(1H-pyrrol-1-yl)-2-[(R)-[(4-methoxy-3-methyl-2-pyridyl)-methyl]sulfinyl]-1H-benzimidazole.

7. The method of claim 3, further comprising: adding the *Burkholderia glathei* or the extract of the *Burkholderia glathei* into a reaction system together with the thioether.

8. The method of claim 7, wherein:

(a) the asymmetrical oxidation is carried out in a buffer solution at pH 7.5-9.0;

(b) a reaction temperature is 15-35° C.;

(c) a reaction time is 4-48 hours;

(d) a concentration of the thioether in the reaction system is 1-100/L; and (e) the thioether is dissolved in a cosolvent, the cosolvent is a water soluble organic solvent, and the cosolvent makes up 2-15% of the reaction system by volume.

9. The method of claim 8, wherein, the pH of the buffer solution is 8.0-9.0.

10. The method of claim 3, wherein, the thioether is selected from the following compounds or pharmaceutically acceptable salts of the following compounds:

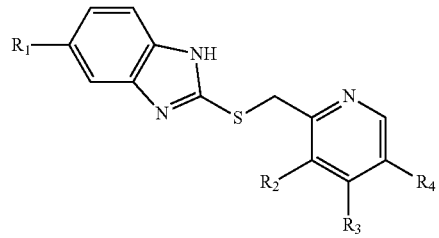

formula I a first compound, having the structure of the formula I, wherein $R_1$ is $CH_3O-$, $R_2$ is $CH_3-$, $R_3$ is $CH_3O-$, and $R_4$ is $CH_3-$;

a second compound, having the structure of the formula I, wherein $R_1$ is H, $R_2$ is $CH_3-$, $R_3$ is $CF_3CH_2O-$, and $R_4$ is H;

a third compound, having the structure of the formula I, wherein $R_1$ is $F_2CHO-$, $R_2$ is $CH_3O-$, $R_3$ is $CH_3O-$, and $R_4$ is H;

a fourth compound, having the structure of the formula I, $R_1$ is H, $R_2$ is $CH_3-$, $R_3$ is $CH_3-O-CH_2-CH_2-CH_2O-$, and $R_4$ is H; and a fifth compound, having the structure of the formula I, $R_1$ is $R_2$ is $CH_3-$,

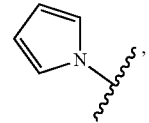 [SMILES: *n1cccc1]

$R_3$ is $CH_3O-$, and $R_4$ is H.

11. The method of claim 4, wherein, the thioether is selected from the following compounds or pharmaceutically acceptable salts of the following compounds:

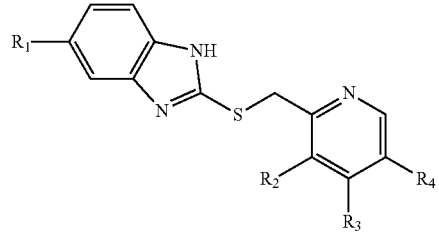

formula I a first compound, having the structure of the formula I, wherein $R_1$ is $CH_3O-$, $R_2$ is $CH_3-$, $R_3$ is $CH_3O-$, and $R_4$ is $CH_3-$;

a second compound, having the structure of the formula I, wherein $R_1$ is H, $R_2$ is $CH_3-$, $R_3$ is $CF_3CH_2O-$, and $R_4$ is H;

a third compound, having the structure of the formula I, wherein $R_1$ is $F_2CHO-$, $R_2$ is $CH_3O-$, $R_3$ is $CH_3O-$, and $R_4$ is H;

a fourth compound, having the structure of the formula I, $R_1$ is H, $R_2$ is $CH_3-$, $R_3$ is $CH_3-O-CH_2-CH_2-CH_2O-$, and $R_4$ is H; and a fifth compound, having the structure of the formula I, $R_1$ is $$\text{[pyrrol-1-yl-CH<]}$$

, $R_2$ is $CH_3$—, $R_3$ is $CH_3O$—, and $R_4$ is H.

12. The method of claim 3, further comprising: adding the extract of the *Burkholderia glathei* into a reaction system together with the thioether.

13. The method of claim 4, further comprising: adding the extract of the *Burkholderia glathei* into a reaction system together with the thioether.

\* \* \* \* \*